(12) United States Patent
Patterson

(10) Patent No.: US 6,191,334 B1
(45) Date of Patent: Feb. 20, 2001

(54) PERFORATION REPAIR DEVICE AND METHOD

(75) Inventor: Matthew C. Patterson, Minneapolis, MN (US)

(73) Assignee: Acoustic Technologies Inc., Northfiedl, MN (US)

( * ) Notice: Under 35 U.S.C. 154(b), the term of this patent shall be extended for 0 days.

(21) Appl. No.: 09/262,153

(22) Filed: Mar. 3, 1999

(51) Int. Cl.$^7$ ........................................... A61F 13/00
(52) U.S. Cl. ..................... 602/41; 128/200.24; 128/858
(58) Field of Search ................... 602/41, 54, 56, 602/58; 128/200.24, 207.18, 858

(56) References Cited

U.S. PATENT DOCUMENTS

| | | |
|---|---|---|
| 4,378,802 | 4/1983 | Ersek . |
| 4,588,400 | * 5/1986 | Ring et al. . |
| 4,592,357 | 6/1986 | Ersek . |
| 4,650,488 | 3/1987 | Bays et al. . |
| 5,350,580 | 9/1994 | Muchow et al. . |
| 5,584,799 | 12/1996 | Gray . |

\* cited by examiner

*Primary Examiner*—Michael A. Brown
*Assistant Examiner*—Lalita Hamilton
(74) *Attorney, Agent, or Firm*—Merchant & Gould P.C.

(57) ABSTRACT

A dissolvable repair device, and a method utilizing the same, that is intended to aid in the repair and healing of a perforation in body tissue, such as a nasal septum. The repair device is intended to be placed over the area of the perforation to act as a scaffolding for the regrowth of tissue over the perforation. The repair device is made from a bioerodable material that is dissolvable upon exposure to certain fluids, including body fluids. Over time, the repair device will dissolve, allowing sufficient time for tissue to regrow over the area of the perforation. Since the repair device is dissolvable, a surgical procedure is not required in order to remove the repair device.

6 Claims, 2 Drawing Sheets

PERFORATION REPAIR DEVICE AND METHOD

FIELD OF THE INVENTION

The invention relates to the field of perforation repair in body tissues, and more particularly relates to a dissolvable device and a method utilizing the dissolvable device, for repairing perforations in body tissues. The dissolvable repair device and associated method have particular use for repairing perforations in nasal septums, as well as in the repair of fistulas that form between the maxillary sinus and the oral cavity.

BACKGROUND OF THE INVENTION

The septum is a structure that separates the two nasal passages within the nose. The septum consists of cartilage anteriorly and bone posteriorly, which are sandwiched between nasal mucosa. Perforations or holes in the nasal septum may result from trauma, infection or exposure to certain drugs such as cocaine. Perforations may also result from medical illnesses such as Wegener's Granulomatosis, or after septoplasty surgery to straighten or repair the nasal septum. The consequences of a perforated nasal septum include the chronic accumulation of crusts and scabs within the nose which obstruct nasal breathing; recurrent epistaxis or nose bleeds from the edge of the perforations; and abnormal airflow through the perforation(s) resulting in a whistling sound as the patient breathes.

The repair of septal perforations is very difficult, with such procedures often times failing and the perforation recurring and even becoming larger as a result of the attempted repair. One conventional repair procedure involves the rotation of flaps of nasal mucosa to cover the perforation(s).

An additional perforation or hole that can form in body tissue comprises fistulas that may form between the maxillary sinus and the oral cavity. Fistulas or connections often times result from infections of the tooth sockets after the extraction of teeth. Fistulas can be extremely difficult to close, and surgical repair is difficult and often fails repeatedly.

The present invention provides an alternative to existing measures for repairing septal perforations, fistulas and other perforations in body tissues.

SUMMARY OF THE INVENTION

The invention provides a dissolvable repair device, and a method utilizing the same, that is intended to aid in the repair and healing of a perforation in body tissue, such as a nasal septum. The repair device is intended to be placed over the area of the perforation to act as a scaffolding for the regrowth of tissue over the perforation. The repair device is made from a bioerodable material that is dissolvable upon exposure to certain fluids, including body fluids. Over time, the repair device will dissolve, allowing sufficient time for tissue to regrow over the area of the perforation. Since the repair device is dissolvable, a surgical procedure is not required in order to remove the repair device.

In one embodiment in accordance with the invention, a perforation repair device is provided which comprises a member made from a bioerodable material. The member is in the form of a sheet having a thickness of between about 0.25 mm and about 2.0 mm.

In another embodiment in accordance with the invention, a method of repairing a perforation in body tissue is provided. The method comprises placing a member made from a bioerodable material over the perforation in the body tissue, securing the member in place over the perforation, and allowing the member to dissolve over a period of time.

The preferred bioerodable material that is used to form the member is collagen, which is a natural architectural component of the tissues of the human body. The collagen can be in the form of a gelatin material that is prepared and manufactured in various ways, thus allowing for the creation of a generally rigid, but slightly malleable device that has some elasticity and memory of structure. These characteristics allow for the device to be temporarily deformed upon the application of a significant force during the positioning of the device. However, in the absence of the force, the device will return to its original configuration, thus providing a generally straight, generally planar support device over which body tissue, such as mucosa, can grow, thereby closing a perforation. One suitable gelatin material is called GELFILM®.

Another advantage of the dissolvable repair device is that it can be impregnated with various materials that enhance the capabilities of the repair device. In one version, the bioerodable material can be impregnated with gluteraldehyde to vary the rate at which the repair device dissolves. Thus, the repair device can be designed to remain for a sufficient time to allow the desired amount of tissue growth over the perforation to occur. The bioerodable material can also be impregnated with antibiotics which will be released in the area of the perforation as the repair device dissolves, thereby assisting in the prevention of infection.

A variety of additional advantages of the invention will be set forth in part in the description which follows, and in part will be obvious from the description, or may be learned by practice of the invention. The advantages of the invention will be realized and attained by means of the elements and combinations particularly pointed out in the claims. It is to be understood that both the foregoing general description and the following detailed description are exemplary and explanatory only and are not restrictive of the invention as claimed.

BRIEF DESCRIPTION OF THE DRAWINGS

Referring now to the drawings wherein like reference numerals indicate corresponding parts throughout the several views.

DETAILED DESCRIPTION OF THE PREFERRED EMBODIMENTS

The invention relates to a device for repairing a perforation in body tissue in either a human or an animal. The device is provided in the form of a thin, sheet-like member made from a bioerodable material. In use, the bioerodable material is secured in place over the perforation and acts a scaffolding for the regrowth of tissue over the perforation. Since the device is made from a bioerodable material, it will dissolve over time once implanted in the body, so that a removal procedure is not required.

The invention further relates to a method of repairing a perforation in body tissue. The method could be practiced on either a human or an animal. The method involves placing a member made from a bioerodable material over the perforation, securing the member in place, and allowing the member to dissolve over a period of time. The member acts as scaffolding for tissue regrowth over the perforation, and as tissue regrowth occurs, the member will dissolve. Eventually the member will completely dissolve, at which point sufficient time has been provided for the tissue to regrow over the entire perforation.

Since the repair device acts as scaffolding, it must be made generally stiff and rigid to enable the repair device to maintain its generally planar configuration once it is implanted and provide support for the tissue regrowth over the perforation. Thus, the repair device of the invention is intended to maintain its generally flat, generally planar configuration after implantation.

Figure 1:
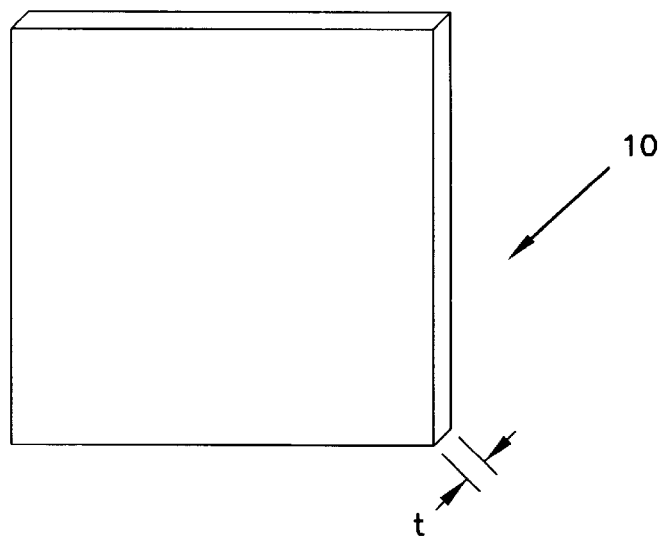
FIG. 1 is a perspective view of the repair device in accordance with the principles of the invention.
Figure 2:
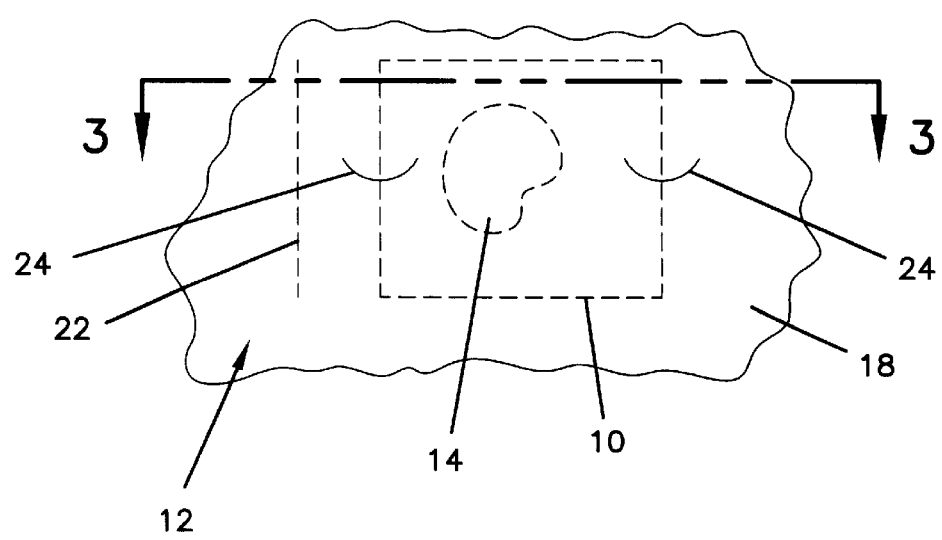
FIG. 2 is a partial side view of a nasal septum showing the repair device in place over a perforation.
Figure 3:
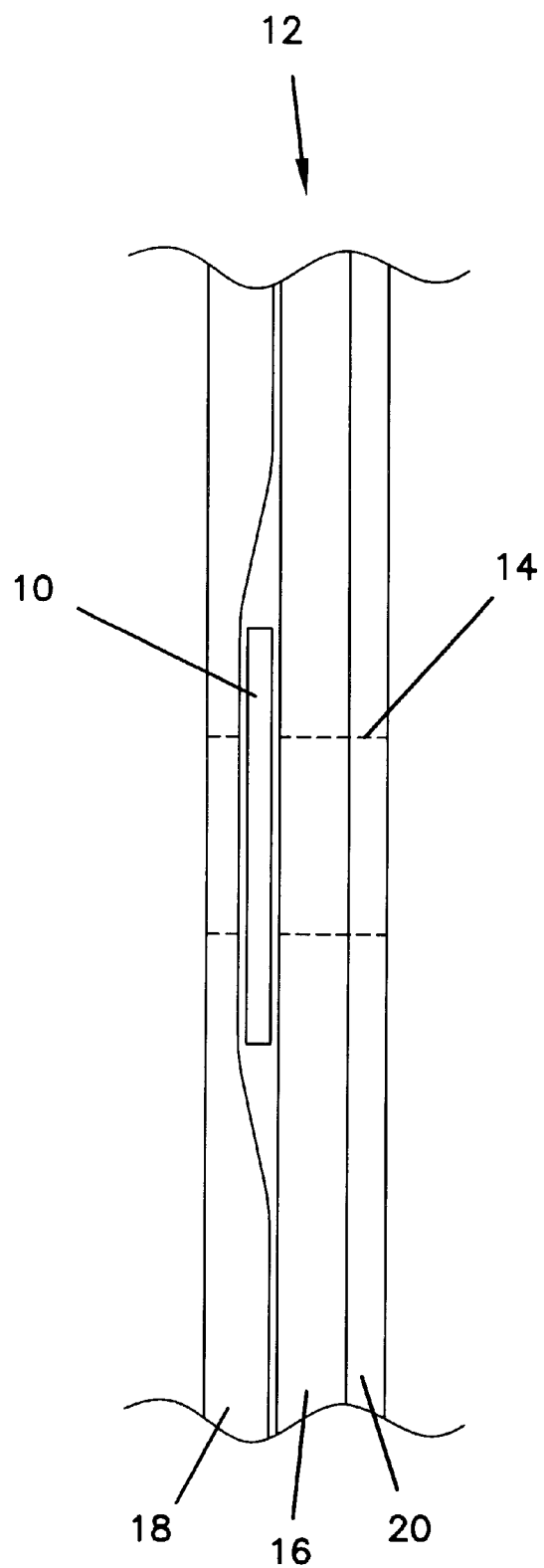
FIG. 3 is a cross-sectional view taken along line 3—3 in FIG. 2, showing the placement of the repair device relative to the layers of the nasal septum.

The preferred implementation of the invention is illustrated in FIGS. 1–3, with the repair device being generally referenced by the reference numeral 10. The repair device 10 is preferably provided in the form of a generally rigid, planar, rectangular, solid sheet made from a bioerodable material. The sheet is preferably formed oversized to enable the surgeon to trim the sheet with a surgical scissors, or the like, and thereby adjust the shape and size of the device 10 to the final, implantable shape and size. The final, implantable shape and size of the device will be dictated by the size, as well as the location of, the perforation. For example, a suitable size for the sheet, prior to trimming, could be about 6.0 cm by about 6.0 cm, such a size being sufficient for use with most perforations. It is to be realized, however, that the sheet could have other dimensions as well. Furthermore, the sheet could have shapes other than rectangular, such as circular, triangular, etc., and still be within the scope of the invention. However, it is to be realized that the sheet could be formed in its final, implantable shape and size, thereby eliminating the trimming step. The sheet has a generally uniform thickness t of between about 0.25 mm and about 2.0 mm.

In the preferred embodiment of the invention, the repair device 10 is made of a material which is bioerodable over a period of time upon exposure to body fluids such as mucus. The dissolution time of the repair device 10 is preferably sufficient to enable tissue growth to occur over the perforation that is being repaired.

The repair device 10 is made with a sufficient stiffness to enable the repair device 10 to generally maintain its planar configuration when implanted over the perforation, and thereby provide support for tissue regrowth over the perforation.

Preferably, the bioerodable material that is used to form the repair device 10 is collagen, a naturally occurring protein. The collagen is preferably in the form of a gelatin material thus providing for a generally firm repair device 10, such that the repair device substantially maintains its planar configuration. The properties of gelatin also allow for the device to be temporarily deformed upon the application of a significant force during the positioning of the repair device. In the absence of such a force, the elastic properties of the collagen allow for the repair device to return to its original, generally planar configuration.

A preferred gelatin collagen material is called GEL-FILM® which is made by the UpJohn Company of Kalamazoo, Mich. GELFILM® is a material that has been used for many years safely in the middle ear to provide temporary support to structures that have been surgically repaired. GELFILM® is dissolvable over a period of time and its components (collagen, water and nitrogen) are reabsorbed by the body without sequelae. In other forms, the repair device 10 is to be made of other forms of collagen and gelatin, not specifically GELFILM®.

The bioerodable material that is used to form the repair device 10 can also be impregnated with various material(s). The repair device 10 can be impregnated with a gluteraldehyde to alter the rate at which the repair device 10 dissolves. In this manner, different sheets can be formed, each having a different dissolution time, thereby enabling the surgeon to select the sheet that would likely remain in place for a length of time to permit tissue growth over the perforation. The repair device 10 can also be impregnated with antibiotics which are released as the repair device dissolves to assist in the prevention of infection in the area of the implanted repair device. The gluteraldehydes and the antibiotics can be used separately, in combination, or not at all, in the repair device, depending upon the requirements of the surgeon.

The bioerodable material forming the repair device 10 is also preferably dissolvable in certain solvents. Such solvents could be used to irrigate the location of the implanted repair device, if accessible, thereby promoting the dissolution of the repair device 10. One suitable solvent is saline. If the physician wishes to have the repair device dissolve more quickly, saline irrigation can be performed to increase the dissolution rate of the repair device.

One specific use of the repair device 10 will now be described with reference to FIGS. 2 and 3, which illustrate the repair device 10 in place on a nasal septum 12 for repairing a perforation 14 in the septum 12. As FIG. 3 shows, the septum 12 comprises a central cartilage layer 16, with a layer 18, 20 of mucosa on each side of the cartilage layer 16. The perforation 14 or hole extends through the layers 16, 18, 20.

The preferred approach to repairing the perforation 14 is to place the repair device 10 in the septum 12 using a standard septoplasty incision 22 in one of the mucosal layers, such as the layer 18. Prior to insertion, the repair device 10 is trimmed by the surgeon to the desired size and shape. The repair device 10 is then inserted through the incision 22 and placed between the mucosal layer 18 and the cartilage layer 16 such that it covers the perforation 14. Dissolvable sutures 24 are then placed through the layers of the septum 12 and the repair device 10 to secure the repair device 10 in place over the perforation 14. To promote the growth of tissue, in this case mucosa, across the area of the perforation, the edges of the perforation can be refreshed using a sharp instrument. Once the repair device 10 is properly located and secured, the incision 22 is then closed.

As described earlier, the repair device 10 can be impregnated with a gluteraldehyde to increase the dissolution time of the repair device, and/or the repair device can be impregnated with an antibiotic so that the antibiotic is released as the repair device dissolves, thereby assisting in the prevention of infection.

The implanted repair device 10 thus acts as a scaffolding for the growth of mucosa over the perforation 14. Over time, the repair device 10, along with the sutures 24, will dissolve, leaving only the tissue that has grown over the perforation to provide closure to the perforation.

While the repair device 10 has been specifically described and shown as repairing a perforation in a nasal septum, the repair device has applications in other perforation repair procedures as well. For instance, the repair device could be used to repair a fistula that has formed between the maxillary sinus and the oral cavity. The repair device can also be used to assist the body in closing any perforation in the upper or lower aerodigestive tracts, or in the ear.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A nasal perforation repair device, consisting essentially of:
   a member made from a bioerodable collagen material, said member being in the form of a sheet having a thickness of between about 0.25 mm and about 2.0 mm.

2. The nasal perforation repair device according to claim 1, wherein the sheet member is generally planar and generally rigid.

3. The nasal perforation repair device according to claim 1, wherein the collagen is in the form of a gelatin material.

4. The nasal perforation repair device according to claim 1, wherein the bioerodable material is impregnated with gluteraldehyde.

5. The nasal perforation repair device according to claim 1, wherein the bioerodable material is impregnated with an antibiotic.

6. The nasal perforation repair device according to claim 1, wherein the sheet is generally rectangular.

* * * * *